United States Patent [19]

Dirlam

[11] 4,012,385

[45] Mar. 15, 1977

[54] ANTIBACTERIAL QUINOXALINE 1,4-DIOXIDES

[75] Inventor: John P. Dirlam, Gales Ferry, Conn.

[73] Assignee: Pfizer Inc., New York, N.Y.

[22] Filed: Aug. 6, 1975

[21] Appl. No.: 602,480

[52] U.S. Cl. .................... 260/250 QN; 424/250; 426/532

[51] Int. Cl.² .................................. C07D 241/52

[58] Field of Search ............... 260/250 Q, 250 QN

[56] References Cited

OTHER PUBLICATIONS

Haddin, et al., Tetrahedron 30, 659 (1974).

Primary Examiner—Donald G. Daus
Assistant Examiner—Mark L. Berch
Attorney, Agent, or Firm—Connolly and Hutz

[57] ABSTRACT

2-Benzoylquinoxaline 1,4-dioxide derivatives, which also have a hydroxymethyl, formyloxymethyl, alkanoyloxymethyl, alkanoylthiomethyl, alkylthiomethyl, alkylsulfinylmethyl or alkylsulfonylmethyl group at the 3-position. The compounds are useful as antibacterial agents.

9 Claims, No Drawings

ANTIBACTERIAL QUINOXALINE 1,4-DIOXIDES

BACKGROUND OF THE INVENTION

1. Field of the Invention

This invention relates to certain novel chemical compounds which have useful antibacterial properties, and which are also of value by virtue of their ability to promote growth when administered to farm animals. More specifically, these new chemical compounds are identified as derivatives of quinoxaline 1,4-dioxide, which have a benzoyl or substituted benzoyl group at the 2-position, and a hydroxymethyl, formyloxymethyl, alkanoyloxymethyl, alkanoylthiomethyl, alkylthiomethyl, alkylsulfinylmethyl, or alkylsulfonylmethyl group at the 3-position.

2. Description of the Prior Art

Quinoxaline 1,4-dioxides are a well-known class of chemical compounds, some of which are known to have antibacterial properties and/or to be useful as growth promoting agents in farm animals. British patent Specification No. 1,134,729 discloses 2-benzoyl-3-alkylquinoxaline 1,4-dioxides and 2-(substituted benzoyl)-3-alkylquinoxaline 1,4-dioxides. 2-Alkanoyl-3-(α-hydroxy lower alkyl)quinoxaline 1,4-dioxides and 2-alkanoyl-3-(α-lower alkanoyloxy lower alkyl)-quinoxaline 1,4-dioxides fall within the broad generic disclosure of U.S. Pat. No. 3,344,022. Edwards, Bambury and Ritter, in the *Journal of Medicinal Chemistry*, 18,637 (1975), describe the preparation and antibacterial activity of 1-hydroxy-1,3-dihydrofuro[3,4-b]quinoxaline 4,9-dioxide.

SUMMARY OF THE INVENTION

It is an object of this invention to provide novel quinoxaline 1,4-dioxides of the formula

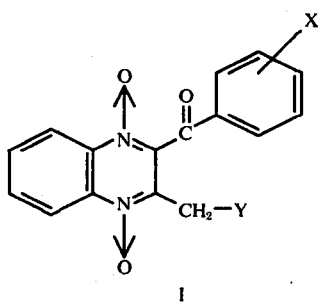

I

Wherein

X is selected from the group consisting of hydrogen, hydroxy, nitro, fluoro, chloro, bromo, alkyl having from one to five carbon atoms and alkoxy having from one to five carbon atoms;

and Y is selected from the group consisting of hydroxy, formyloxy, alkanoyloxy having from two to six carbon atoms, alkanoylthio having from two to six carbon atoms, alkylthio having from one to five carbon atoms, alkylsulfinyl having from one to five carbon atoms and alkylsulfonyl having from one to five carbon atoms;

said quinoxaline 1,4-dioxide compounds of formula I being of value as antibacterial agents and agents for promoting growth in farm animals.

The preferred quinoxaline 1,4-dioxide compounds of the formula I are those compounds wherein X is hydrogen. Especially preferred compounds of formula I are the compounds wherein X is hydrogen and Y is hydroxy, the said alkanoyloxy, the said alkanoylthio or the said alkylsulfonyl.

Particularly desirable individual compounds of the formula I are:

2-benzoyl-3-hydroxymethylquinoxaline 1,4-dioxide,
2-benzoyl-3-acetoxymethylquinoxaline 1,4-dioxide,
2-benzoyl-3-methylsulfonylmethylquinoxaline 1,4-dioxide and
2-benzoyl-3-acetylthiomethylquinoxaline 1,4-dioxide.

It is a further object of this invention to provide certain novel transformation products of the compounds of formula I, wherein Y is hydroxy. These novel transformation products are 1,3-dihydrofuro[3,4-b]quinoxaline 4,9-dioxides of formula

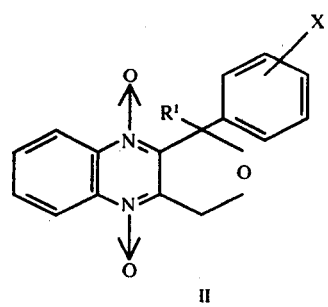

II wherein

X is selected from the group consisting of hydrogen, hydroxy, nitro, fluoro, chloro, bromo, alkyl having from one to five carbon atoms and alkoxy having from one to five carbon atoms;

and $R^1$ is alkoxy having from one to five carbon atoms;

said novel 1,3-dihydrofuro[3,4-b]quinoxaline 4,9-dioxides of formula II also being of value as antibacterial agents and agents for promoting growth in farm animals.

The preferred compound of formula II is the compound wherein X is hydrogen and $R^1$ is methoxy.

DETAILED DESCRIPTION OF THE INVENTION

As indicated hereinbefore, it is an object of this invention to provide novel and useful quinoxaline 1,4-dioxide compounds of formula I. In one method, according to the invention, the novel compounds of formula I can be prepared from the appropriate compound of formula III, wherein X is as previously defined.

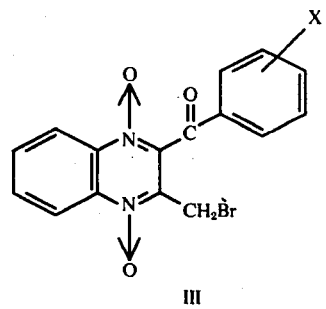

III

Thus, the compounds of formula I, wherein Y is hydroxy, are prepared by hydrolysis of a compound of formula III. That is to say, the compound of formula III is treated with water. Although use of as low as about five molar equivalents of water, based on bromo compound, will successfully lead to the formation of the compound of formula I, wherein Y is hydroxy, it is common to use a large excess of water. Indeed, it is common to use a sufficient amount of water that it is not necessary to use another reaction solvent. However, a co-solvent which is miscible with water, which will dissolve the compound of formula III, and which does not adversely interact with either the starting material or the final product can be used. Examples of such solvents are ethers, such as tetrahydrofuran, dioxan and 1,2-dimethoxyethane, and amides, such as N,N-dimethylformamide and N-methylpyrrolidone. The hydrolysis reaction is normally carried out at a temperature in the range from about 50° C. to 150° C., and preferably at about 100° C. At about 100° C. the reaction takes several hours, e.g. about 12 hours, to proceed substantially to completion. As will be appreciated by one skilled in the art, the reaction proceeds more quickly at higher temperatures and more slowly at lower temperatures. The reaction product is recovered by standard methods. If the product is out of solution at the end of the reaction, it can be recovered by filtration. Alternatively, if the product remains dissoled at the end of the reaction, it can be recovered by evaporation, or by solvent extraction, according to standard procedures.

The compounds of formula I, wherein Y is formyloxy, alkanoyloxy or alkanoylthio are prepared by reaction of the requisite compound of formula III with a salt of formic acid or the appropriate alkanoic or thiolalkanoic acid. The reaction is usually carried out by contacting the reactants in a reaction-inert organic solvent, and a temperature in the range from about 0° C. to about 80° C., and preferably from about 20° C. to about 40° C. Appropriate solvents are those which will serve to dissolve one, and preferably both, of the reactants, and will not adversely interact with either the starting reagents or the product. Examples of such solvents are ethers, such as diethyl ether, tetrahydrofuran, dioxan and mono- and dialkyl ethers of ethylene glycol, propylene glycol and diethylene glycol; lower alkanols, such methanol, ethanol and isopropanol; halogenated hydrocarbons, such as methylene chloride and chloroform; tertiary amides, such as N,N-dimethylformamide, N,N-dimethylacetamide and N-methylpyrrolidone; acetonitrile; and mixtures of these solvents.

A wide variety of salts of the formic, alkanoic or thioalkanoic acid can be used, and examples of salts which can be used are: alkaline metal salts, such as sodium and potassium salts; alkaline earth metal salts, such as calcium and barium salts; and tertiary amine salts, such as triethylammonium, N-methylmorpholinium and N,N-dimethylanilinium salts. The choice of a particular salt is not usually critical, although selection of a salt which is soluble in the particular solvent being used will normally speed up the rate of reaction. It is usual therefore, when using a salt which is soluble in the solvent system chosen, to use relatively short reaction times and relatively low reaction temperatures.

The time course of the reaction varies according to a number of factors, such as the reactivity of the reagents, the concentrations of the reagents, the reaction solvent and the reaction temperature. As will be appreciated by one skilled in the art, the reaction proceeds more quickly at relatively high temperatures and more slowly at relatively low temperatures. Moreover, the salts of the thioalkanoic acids tend to react more quickly than the salts of formic or the alkanoic acids. However, when working at about ambient temperature, reaction times of from about one hour to about twenty-four hours, are commonly used.

A wide variety of reactant ratios are operative in this reaction; however, it is usual to combine the compound of formula III and the formate, alkanoate or thioalkanoate salt in substantially equimolar proportions.

The products of the instant process are isolated from the reaction medium by standard methods. For example, in those instances where the product precipitates during the course of the reaction, it can be recovered simply by filtration. Alternatively, when the product does not precipitate spontaneously, it can often be induced to precipitate at the end of the reaction by dilution of the reaction medium with a non-solvent, such as ether, hexane or water. A further method of product recovery involves removal of the solvents by evaporation, followed by partitioning of the crude product thus obtained between water and a water-immiscible organic solvent. After separation of the two phases, the product-containing phase is evaporated, to yield the product.

The compounds of formula I, wherein Y is alkylthio, are prepared by reaction of the requisite compound of formula III with the appropriate alkyl mercaptan, in the presence of a tertiary amine. Typical examples of tertiary amines which can be used are trimethylamine, triethylamine, tributylamine, N-methylmorpholine, N,N-dimethylaniline, pyridine, quinoline and the like. The reaction times, reaction temperatures, solvents and reactant ratios useful in the instant process are the same as those used in the preparation of the compounds of formula I, wherein Y is formyloxy, alkanoyloxy or alkanoylthio.

The compounds of formula I, wherein Y is alkylsulfinyl, are prepared from the corresponding compounds of formula I, wherein Y is alkylthio, by oxidation. A wide variety of oxidizing agents, known in the art for oxidizing sulfides to sulfoxides, such as, for example, peracids, sodium metaperiodate and 1,4-diazabicyclo[2.2.2]octane dibromide can be used. (See, for example, Szmant and Barnard, Bateman and Cuneen in "Organic Sulfur Compounds," edited by Kharasch, Pergamon Press, 1961, pages 154 and 229; Oae et al., *Bulletin of the Chemical Society of Japan*, 39, 364 [1966]. However, a particularly convenient oxidant, useful in the process for oxidizing a compound of formula I, wherein Y is alkylthio, to a compound of formula I, wherein Y is alkylsulfinyl, is m-chloroperbenzoic acid. When the latter oxidant is used, the compound of formula I is contacted with from about 0.8 to about 1.2 molar equivalents of m-chloroperbenzoic acid, in a reaction-inert organic solvent, at a temperature in the range from about 20° C. to about 100° C., and preferably from about 30° C. to about 50° C. until consumption of the oxidant is substantially complete. Typical solvents which can be used are chlorinated hydrocarbons, such as chloroform, methylene chloride and ethylene dichloride. At about 50° C., the reaction takes a few hours, e.g. about four hours. The reaction mixture is then washed with sodium carbonate, to remove the m-chlorobenzoic acid, and the product is recovered by evaporation of the solvent.

In like manner, the compounds of formula I, wherein Y is alkylsulfonyl, are also prepared from the corresponding compounds of formula I, wherein Y is alkylthio, by oxidation. In this instance reagents and conditions known in the art for oxidizing sulfides to sulfones are chosen (see, for example, Szmant, and Barnard, Batement and Cuneen, in "Organic Sulfur Compounds," edited by Kharasch, Pergamon Press, 1961, pages 154 and 229). m-Chloroperbenzoic acid can conveniently be used to oxidize a compound of formula I, wherein Y is alkylthio to a compound wherein Y is alkysulfonyl. The method described above for the oxidation of a compound of formula I, wherein Y is alkylthio, to a compound wherein Y is alkylsulfinyl can be used, except that it is necessary to use at least two, and preferably about three, molar equivalents of m-chloroperbenzoic acid for each molar quantity of sulfide.

As will be appreciated by one skilled in the art, the compounds of formula I, wherein Y is alkylsulfonyl, can also be prepared by oxidation of the appropriate compounds of formula I, wherein Y is alkylsulfinyl. Conditions known in the art for oxidizing sulfoxides to sulfones can be used for this purpose. In particular, treatment of a compound of formula I, wherein Y is alkylsulfinyl, with at least one molar equivalent of m-chloroperbenzoic acid, using the conditions previously described for conversion of a compound of formula I, wherein Y is alkylthio, into a compound of formula I, wherein Y is alkylsulfinyl, leads to the formation of a compound of formula I, wherein Y is alkylsulfonyl.

As indicated hereinbefore, a further object of this invention is to provide certain novel transformation products of the compounds of formula I, wherein Y is hydroxy. The said novel transformation products are 1,1-disubstituted-1,3 -dihydrofuro[3,4-b]quinoxaline 4,9-dioxide compounds of the formula:

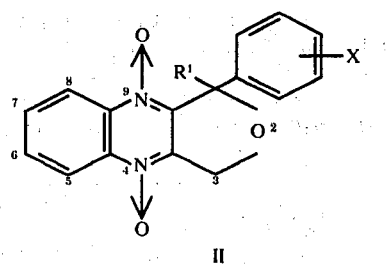

wherein X is selected from the group consisting of hydrogen, hydroxy, nitro, fluoro, chloro, bromo, alkyl having from one to five carbon atoms and alkoxy having from one to five carbon atoms; and $R^1$ is alkoxy having from one to five carbon atoms.

The compounds of formula II are prepared by a process which comprises treating the appropriate compound of formula I, wherein Y is hydroxy, with the requisite alkanol having from one to five carbon atoms, in the presence of an acid catalyst. The reaction is normally carried out by contacting the compound of formula I, wherein Y is hydroxy, with the alkanol, at a temperature in the range from about 0° C. to about 100° C., and preferably at about ambient temperature, in the presence of an acid catalyst. Any acid having a $pK_a$ less than about 2.5 can be used as the catalyst, and typical examples of acids which can be used are hydrogen chloride, hydrogen bromide, methane-sulfonic acid, benzenesulfonic acid, p-toluenesulfonic acid, trifluoroacetic acid and trichloroacetic acid. Generally, the acid is present in an amount from about 0.01 to 1.0 molar equivalents, but amounts larger than one molar equivalent are sometimes used. It is desirable to use an excess, preferably at least five molar equivalents, of the alkanol, and in most instances sufficient alkanol is used to obviate the need for a further solvent. However, a further solvent which is miscible with the alkanol and does not adversely interact with either the starting material or the product can be added, if desired. Typical exampls of such solvents include ether, tetrahydrofuran, dioxan, 1,2-dimethoxymethane, benzene, chloroform and methylene chloride. When working at about ambient temperature the reaction commonly takes from 1 to about 5 days to produce a satisfactory yield of product. The product is isolated by standard methods. For example, in those instances where the product precipitates during the course of the reaction, it can be recovered simply by filtration. Alternatively, when the product does not precipitate spontaneously, it can often be induced to precipitate at the end of the reaction by dilution of the reaction medium with a non-solvent, such as ether, hexane or water. A further method of product recovery involves removal of the solvents by evaporation, followed by partitioning of the crude product thus obtained between water and a water-immiscible organic solvent. After separation of the two phases, the product-containing phase is evaporated, to yield the product.

The compounds of formula II can also be prepared by treating a compound of formula I, wherein Y is formyloxy or alkanoyloxy, with a lower alkanol in the presence of an acid catalyst. The conversion of a compound of formula I, wherein Y is formyloxy or alkanoyloxy, into the corresponding compound of formula II can be carried out using the same catalysts and reaction conditions described for the conversion of a compound of formula I, wherein Y is hydroxy, into the corresponding compound of formula II.

The 3-bromomethyl compounds of formula III, used as starting materials for preparation of the antibacterial agents of this invention, are prepared by bromination of the corresponding 3-methyl compound IV, viz:

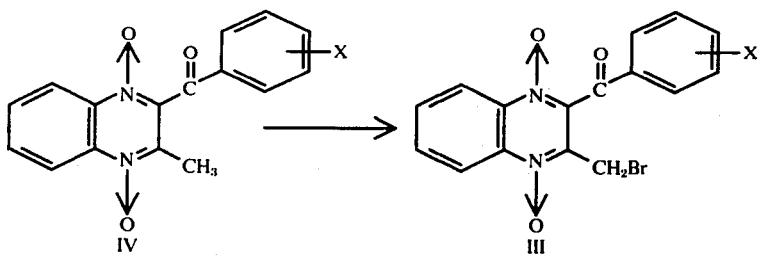

The bromination can be carried out using standard procedures well-known in the art. However, a particularly convenient method comprises treating the compound of formula IV with about two molar equivalents of molecular bromine in refluxing methanol for several hours.

The compounds of formula IV are prepared by condensation of benzofurazan 1-oxide with the appropriate benzoylacetone derivative, viz:

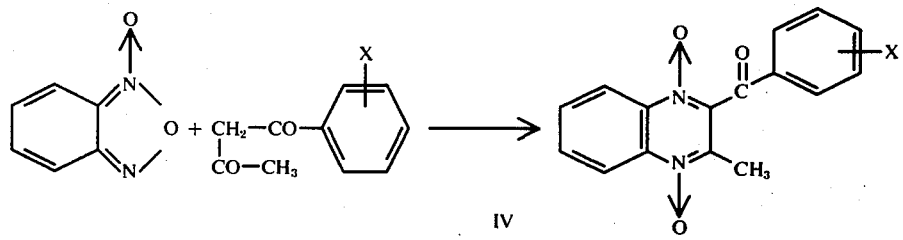

Methods for the condensation of benzofurazan 1-oxide with 1,3-dicarbonyl compounds are well-known. See, for example, British patent specification Nos. 1,134,729 and 1,308,370 and U.S. Pat. No. 3,660,398. The benzoylacetone derivatives used to prepare the compounds of formula IV are either known compounds, which are prepared by the published methods, or they are homologues or isomers of known compounds, which are prepared by methods analogous to the published methods. See, for example, *Chemische Berichte*, 38,693; *Annalen*, 446, 169 (1926); *Journal of Organic Chemistry*, 30, 3000 (1965). Benzofurazan 1-oxide is prepared by the method described in *Organic Syntheses*, Collective Volume IV, John Wiley & Co., 1963, page 74.

The novel quinoxaline 1,4-dioxide and 1,3-dihydrofuro[3,4-b]quinoxaline 4,9-dioxide compounds of formulae I and II, wherein X, Y and $R^1$ are as previously defined, show antibacterial activity in vitro. This in vitro antibacterial activity can be demonstrated by the conventional two-fold serial dilution technique in Brain-Heart Infusion broth (Difco). The broth is inoculated with bacteria, and with the quinoxaline 1,4-dioxide or 1,3-dihydrofuro[3,4-b]quinoxaline 4,9-dioxide, and then it is incubated overnight at 37° C., under anaerobic conditions. On the next day, the test is read visually. The minimum inhibitory concentration (MIC) of test compound is the lowest concentration which prevents turbidity, i.e. which prevents growth of the microorganism. The antibacterial compounds of the invention are active against both gram-positive and gram-negative bacteria, and in particular they are active against *Streptococcus pyogenes*, *Escherichia coli* and *Salmonella choleraesius*. In vitro activities of certain of the compounds of the invention are shown in Table I.

The quinoxaline 1,4-dioxides and 1,3-dihydrofuro[3,4-b]quinoxaline 4,9-dioxides of this invention also show antibacterial activity in vivo. In determining such activity, the test compound is administered to mice which have been infected by intraperitoneal injection of a lethal inoculum of pathogenic bacteria. The test compound is administered using a multiple dosing regimen at a dosage of 25 mg./kg., and using either the oral (PO) or the subcutaneous (SC) route. The inoculum of bacteria varies from one to about ten times the amount needed to kill 100% of the mice, under conditions of the test. At the end of the test, the activity of a compound is assessed by counting the number of survivors among the treated animals and expressing the activity of a compound as the percentage of animals which survive. In Table I, in vivo activities of several of the compounds of this invention against *Salmonella choleraesius* are presented.

TABLE I

| COMPOUND | MIC's (mcg./ml) | | | Percentage protection vs. Sal. Choleraesuis | |
|---|---|---|---|---|---|
| | Strep pyogenes | Esch coli | Sal. Choleraesuis | SC | PO |
| 2-benzoyl-3-acetoxymethyl-quinoxaline 1,4-dioxide | 12.5 | 12.5 | 50 | 10 | 50 |
| 2-benzoyl-3-acetylthio-methylquinoxaline 1,4-dioxides | >200 | >200 | >200 | 20 | 30 |
| 2-benzoyl-3-hydroxy-methylquinoxaline 1,4-dioxide | 0.78 | 1.56 | 6.25 | 60 | 80 |
| 2-benzoyl-3-methylsulfonylmethylquinoxaline- | 12.5 | 25 | 25 | 30 | 60 |

TABLE I-continued

| COMPOUND | MIC's (mcg./ml) | | | Percentage protection vs. Sal. Choleraesuis | |
| --- | --- | --- | --- | --- | --- |
| | Strep pyogenes | Esch coli | Sal. Choleraesuis | SC | PO |
| 1,4-dioxide 1-methoxy-1-phenyl-1,3-dihydrofuro[3,4-b]-quinoxaline 4,9-dioxide | 25 | 25 | 100 | 30 | 30 |

The in vitro antibacterial activity of the quinoxaline 1,4-dioxides of this invention makes them valuable as industrial antimicrobials, for example in water treatment, slime control, paint preservation and wood preservation, as well as for topical application as disinfectants. In the case of use of these compounds for topical application, it is often convenient to admix the active ingredient with a non-toxic carrier, such as vegetable or mineral oil or an emollient cream. Similary, it can be dissolved or dispersed in liquid diluents or solvents such as water, alkanols, glycols or mixtures thereof. In most instances it is appropriate to employ concentrations of active ingredients of from about 0.1 percent to about 10 percent by weight, based on total composition.

The in vivo activity of the quinoxaline 1,4-dioxide compounds of this invention makes them useful for the treatment of bacterial infections, due to susceptible organisms, in animals, particularly swine, cattle and poultry. When used in animals for these purposes, the compounds can be administered orally or parenterally, i.e. intramuscularly, subcutaneously or intraperitioneally, at a dosage of from about 1 mg./kg. of body weight to about 100 mg./kg. of body weight. However, in general, it will be found that a dosage in the range from about 5 mg./kg. of body weight to about 50 mg./kg. of body weight will suffice. The compounds can be administered alone, or they can be combined with various diluents and carriers, according to standard veterinary practice.

When parenteral use of the compounds of this invention is contemplated, they can be combined with vehicles such as water, isotonic saline, isotonic dextrose, Ringer's solution, or non-aqueous diluents such as vegetable oils (cotton seed oil, sesame oil, corn oil) or dimethylsulfoxide. Buffering agents, local anesthetics and/or inorganic salts are commonly added to afford desirable pharmacological properties.

In the case of oral use, the quinoxaline 1,4-dioxides and 1,3-dihydrofuro[3,4-b]quinoxaline 4,9-dioxides of this invention can be combined with various diluents including aqueous diluents, non-aqueous diluents and solid diluents, in the form of capsules, tablets, lozenges, troches, dry mixes, suspensions, solutions and dispersions.

A particularly valuable application of the compounds of this invention is as animal growth promotants. The addition of a low level of one or more of the herein described quinoxaline 1,4-dioxides or 1,3-dihydrofuro[3,4-b]quinoxaline 4,9-dioxides to the diet of healthy animals, both ruminant and non-ruminant, such that these animals receive the product over an extended period of time, at a concentration of from about 1 ppm to about 100 ppm, and usually from about 5 ppm to about 50 ppm., blended with their feed, especially over a major portion of their active growth period, results in an acceleration of the rate of growth and improves feed efficiency. Examples of animals which can be treated in this way are poultry (chickens, ducks, turkeys), cattle sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed. The quinoxaline 1,4-dioxides and 1,3-dihydrofuro[3,4-b]quinoxaline 4,9-dioxides can be blended with the animal's feed, or they can be administered in an equivalent amount via the animal's water ration.

The following Examples are provided solely for the purpose of illustration.

EXAMPLE I

2-Benzoyl-3-hydroxymethylquinoxaline 1,4-Dioxide

A stirred slurry of 10.0 g (0.028 mol.) of 2-benzoyl-3-bromomethylquinoxaline 1,4-dioxide in 1,000 ml. of water was heated under reflux for 18 hours. The hot reaction mixture was filtered, and the filtrate was allowed to cool to 25° C. The solid which precipitated was collected by filtration to provide a first crop of crude product. The aqueous filtrate was extracted with dichloromethane, which was then dried and evaporated in vacuo, to provide a second crop of crude product. The combined crude product was 7.0 g. (85% yield). It was recrystallized from ethanol to give 4.9 g. (59% yield) of 2-benzoyl-3-hydroxymethylquinoxaline 1,4-dioxide having m.p 178°–179° C.

Analysis: Calc'd for $C_{16}H_{12}N_2O_4$ (percent): C, 64.93; H, 4.09; N, 9.46; Found (percent): C, 65.04; H, 4.07; N, 9.19.

EXAMPLE II

Solvolysis of the appropriate 2-(substituted benzoyl)-3-bromomethyl-quinoxaline 1,4-dioxide in water, according to the procedure of Example I, provides the following compounds:

2-(3-hydroxybenzoyl)-3-hydroxymethylquinoxaline 1,4-dioxide,
2-(4-nitrobenzoyl)-3-hydroxymethylquinoxlaine 1,4-dioxide,
2-(2-fluorobenzoyl)-3-hydroxymethylquinoxaline 1,4-dioxide,
2-(3-chlorobenzoyl)-3-hydroxymethylquinoxaline 1,4-dioxide,
2-(4-chlorobenzoyl)-3-hydroxymethylquinoxaline 1,4-dioxide,
2-(4-bromobenzoyl)-3-hydroxymethylquinoxaline 1,4-dioxide,
2-(2-methylbenzoyl)-3-hydroxymethylquinoxaline 1,4-dioxide, 2-(3-isopropylbenzoyl)-3-hydroxymethylquinoxaline 1,4-dioxide,
2-(4-[pentyl]benzoyl)-3-hydroxymethylquinoxaline 1,4-dioxide,
2-(2-methoxybenzoyl)-3-hydroxymethylquinoxaline 1,4-dioxide,
2-(3-methoxybenzoyl)-3-hydroxymethylquinoxaline 1,4-dioxide,
2-(4-methoxybenzoyl)-3-hydroxymethylquinoxaline 1,4-dioxide,
2-(4-ethoxybenzoyl)-3-hydroxymethylquinoxaline 1,4-dioxide and
2-(4-[pentyloxy]benzoyl)-3-hydroxymethylquinoxaline 1,4-dioxide, respectively.

EXAMPLE III

2-Benzoyl-3-acetoxymethylquinoxaline 1,4-Dioxide

To a solution of 3.0 g. (8.4 mmol.) of 2-benzoyl-3-bromomethylquinoxaline 1,4-dioxide and 0.90 g (9.2 mmol.) of potassium acetate in 40 ml. of N,N-dimethylformamide, was added 0.22 g. (1.3 mmol.) of finely ground potassium iodide. The reaction mixture was stirred for 1.5 hours at ambient temperature, and then it was poured into 1,000 ml. of ether. The solid which precipitated was removed by filtration and discarded. Evaporation of the filtrate in vacuo left a yellow solid which was washed with methanol and dried, to give 2.7 g (94% yield) of 2-benzoyl-3-acetoxymethylquinoxaline 1,4-dioxide, m.p. 164°–167° C.

Analysis: Calc'd for $C_{18}H_{14}N_2O_5$ (percent): C, 63.96; H, 4.18; N, 8.29; Found (percent): C, 63.33; H, 4.34; N, 8.48.

EXAMPLE IV

Reaction of 2-benzoyl-3-bromomethylquinoxaline 1,4-dioxide or the appropriate 2-(substituted benzoyl)-3-bromomethylquinoxaline 1,4-dioxide with the potassium salt of the requisite acid, according to the procedure of Example III, produces the following compounds

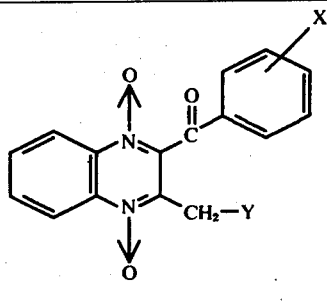

| X | Y |
|---|---|
| H | O—CO—CH₂CH₃ |
| H | O—CO—CH₂CH₂CH₃ |
| H | O—CO—CH₂CH₂CH₂CH₃ |
| H | O—CO—CH₂CH₂CH(CH₃)₂ |
| 3-OH | O—CO—CH₃ |
| 4-NO₂ | O—CO—CH₂CH₃ |
| 2-F | O—CO—CH₃ |
| 3-Cl | O—CO—CH₂CH₂CH₂CH₂CH₃ |
| 4-Cl | O—CO—CH₃ |
| 2-CH₃ | O—CO—CH₃ |
| 3-OCH₃ | O—CO—CH(CH₃)₂ |
| 4-OCH₂CH₃ | O—CO—CH₃ |
| 4-OCH₂CH₂CH(CH₃)₂ | O—CO—CH₃ |
| 4-CH₂CH₂CH₂CH₂CH₃ | O—CO—CH₃ |
| 4-OH | O—CO—H |
| 4-Cl | O—CO—H |
| 4-(CH₃)₂CH | O—CO—H |
| 4-OCH₃ | O—CO—H |

*-continued*

| X | Y |
|---|---|
| 3-NO₂ | O—CO—H |

EXAMPLE V

2-Benzoyl-3-acetylthiomethylquinoxaline 1,4-Dioxide

To a solution of 2.23 g. (6.2 mmol.) of 2-benzoyl-3-bromomethylquinoxaline 1,4-dioxide and 0.48 g. (6.2 mmol.) of thiolacetic acid in 20 ml. of chloroform was added, dropwise, 0.62 g. (6.2 mmol.) of triethylamine. The reaction mixture was stirred at ambient temperature overnight, and then it was washed with water. The chloroform solution was then dried and evaporated in vacuo, leaving a yellow solid. The yellow solid was washed with methanol, and dried, which afforded 1.35 g. (62% yield) of 2-benzoyl-3-acetylthiomethylquinoxaline 1,4-dioxide, having m.p. 180°–181° C.

Analysis: Calc'd for $C_{18}H_{14}N_2O_4S$ (percent): C, 61.07; H, 3.99; N, 7.91; Found (percent): C, 60.64; H, 4.05; N, 7.83.

EXAMPLE VI

Reaction of 2-benzoyl-3-bromomethylquinoxaline 1,4-dioxide or the appropriate 2-(substituted benzoyl)-3-bromomethylquinoxaline 1,4-dioxide with the requisite alkanoic or thiolalkanoic acid, according to the procedure of Example V, produces the following compounds:

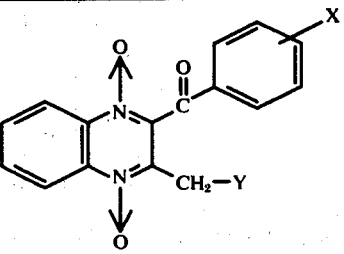

| X | Y |
|---|---|
| H | S—CO—CH₂CH₃ |
| H | S—CO—CH(CH₃)₂ |
| H | S—CO—CH₂CH(CH₃)₂ |
| H | S—CO—CH₂CH₂CH₂CH₂CH₃ |
| H | S—CO—CH₂CH₂CH(CH₃)₂ |
| 3-OH | S—CO—CH₂CH₂CH(CH₃)₂ |
| 3-NO₂ | S—CO—CH₃ |
| 3-Cl | S—CO—CH₂CH₂CH₃ |
| 4-Cl | S—CO—CH₃ |
| 4-Br | S—CO—CH₃ |
| 2-CH₂CH₃ | S—CO—CH₂CH₃ |
| 2-OCH₃ | S—CO—CH₂CH₂CH₃ |
| 3-OCH₃ | S—CO—CH₃ |
| H | O—CO—CH₃ |
| H | O—CO—CH₂CH₃ |
| 4-Cl | O—CO—CH(CH₃)₂ |
| 4-OCH₃ | O—CO—CH₃ |
| 4-OH | O—CO—CH₃ |

-continued

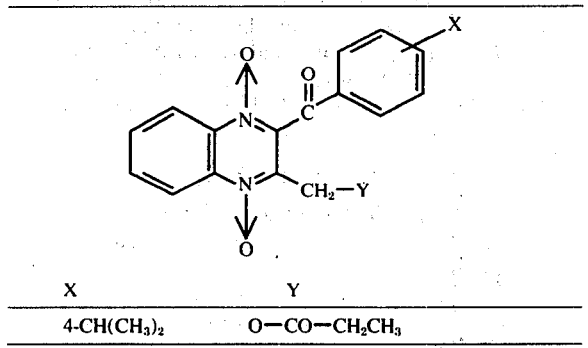

| X | Y |
|---|---|
| 4-CH(CH₃)₂ | O—CO—CH₂CH₃ |

EXAMPLE VII

2-Benzoyl-3-methylthiomethylquinoxaline 1,4-Dioxide

An excess of methyl mercaptan was bubbled into a solution of 1.0g. (2.8 mmol.) of 2-benzoyl-3-bromomethylquinoxaline 1,4-dioxide in 20 ml. of chloroform. To the resulting solution was added 3.1 g (3.1 mol.) of triethylamine, and the reaction mixture was stirred at ambient temperature overnight. The chloroform was washed with water, dried, and evaporated leaving 0.72 g. (80% yield) of crude 2-benzoyl-3-methylthiomethylquinoxaline 1,4-dioxide, m.p. 130°–137+ C. Examination of the crude product by nuclear magnetic resonance spectroscopy revealed that the product was contaminated by about 20% of 2-benzoyl-3-methylquinoxaline 1,4-dioxide. The product can be purified further by chromatography if desired.

EXAMPLE VIII

Reaction of 2-benzoyl-3-bromomethylquinoxaline 1,4-dioxide or the appropriate 2-(substituted benzoyl)-3-bromomethylquinoxaline 1,4-dioxide with the requisite mercaptan, according to the procedure of Example VII, produces the following compounds:

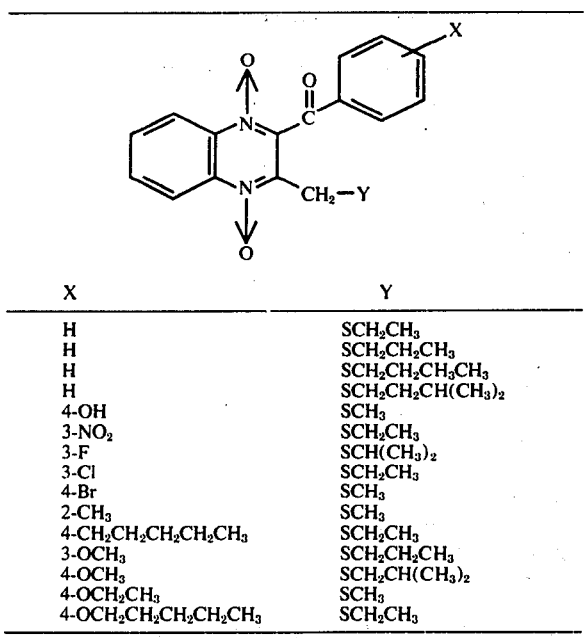

| X | Y |
|---|---|
| H | SCH₂CH₃ |
| H | SCH₂CH₂CH₃ |
| H | SCH₂CH₂CH₃CH₃ |
| H | SCH₂CH₂CH(CH₃)₂ |
| 4-OH | SCH₃ |
| 3-NO₂ | SCH₂CH₃ |
| 3-F | SCH(CH₃)₂ |
| 3-Cl | SCH₂CH₃ |
| 4-Br | SCH₃ |
| 2-CH₃ | SCH₃ |
| 4-CH₂CH₂CH₂CH₂CH₃ | SCH₂CH₃ |
| 3-OCH₃ | SCH₂CH₂CH₃ |
| 4-OCH₃ | SCH₂CH(CH₃)₂ |
| 4-OCH₂CH₃ | SCH₃ |
| 4-OCH₂CH₂CH₂CH₂CH₃ | SCH₂CH₃ |

EXAMPLE IX

2-Benzoyl-3-methylsulfinylmethylquinoxaline 1,4-Dioxide

A solution of 3.26 g. (0.01 mol) of 2-benzoyl-3-methylthiomethylquinoxaline 1,4-dioxide and 2.20 g. (0.01 mol.) of 85% pure 3-chloroperbenzoic acid in 150 ml. of chloroform is stirred at room temperature overnight. The reaction mixture is washed with 5% sodium bicarbonate solution, dried, and evaporated in vacuo to afford crude 2-benzoyl-3-methylsulfinylmethylquinoxaline 1,4-dioxide.

EXAMPLE X

Oxidation of the appropriate 2-benzoyl-3-alkylthiomethylquinoxaline 1,4-dioxide or 2-(substituted benzoyl)-3-alkylthiomethylquinoxaline 1,4-dioxide with one equivalent of 3-chloroperbenzoic acid, according to the procedure of Example IX, affords the following compounds:

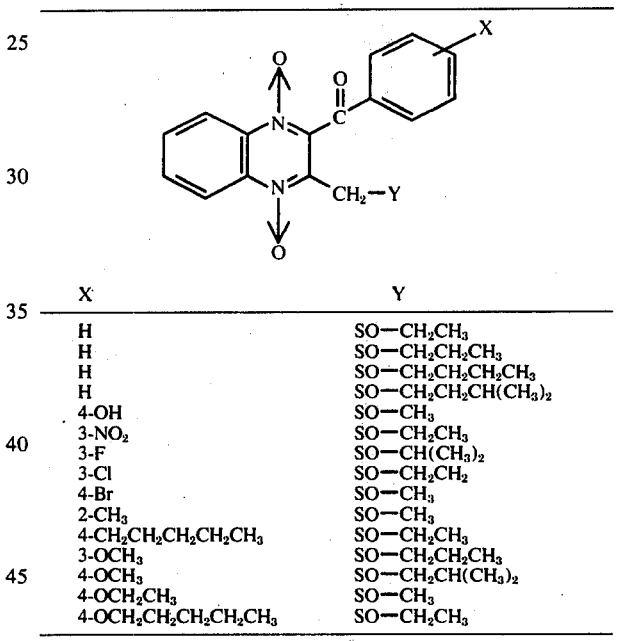

| X | Y |
|---|---|
| H | SO—CH₂CH₃ |
| H | SO—CH₂CH₂CH₃ |
| H | SO—CH₂CH₂CH₂CH₃ |
| H | SO—CH₂CH₂CH(CH₃)₂ |
| 4-OH | SO—CH₃ |
| 3-NO₂ | SO—CH₂CH₃ |
| 3-F | SO—CH(CH₃)₂ |
| 3-Cl | SO—CH₂CH₂ |
| 4-Br | SO—CH₃ |
| 2-CH₃ | SO—CH₃ |
| 4-CH₂CH₂CH₂CH₂CH₃ | SO—CH₂CH₃ |
| 3-OCH₃ | SO—CH₂CH₂CH₃ |
| 4-OCH₃ | SO—CH₂CH(CH₃)₂ |
| 4-OCH₂CH₃ | SO—CH₃ |
| 4-OCH₂CH₂CH₂CH₂CH₃ | SO—CH₂CH₃ |

EXAMPLE XI

2-Benzoyl-3-methylsulfonylmethylquinoxaline 1,4-Dioxide

A solution of 0.72 g. (2.2 mmol.) of 2-benzoyl-3-methylthiomethylquinoxaline 1,4-dioxide and 1.09 g. (5.4 mmol.) of 85% 3-chloroperbenzoic acid in 20 ml. of chloroform was stirred at room temperature overnight. The reaction mixture was washed with 5% sodium bicarbonate solution, dried, and evaporated in vacuo, to afford crude 2-benzoyl-3-methylsulfonylmethylquinoxaline 1,4-dioxide as a liquid. Recrystallization of this crude product from ether gave 0.47 g. (60% yield) of the title compound as a solid, m.p. 209°–211° C.

Analysis: Calc'd. for $C_{17}H_{14}N_2O_5S$ (percent): C, 57.04; H, 3.94; N, 7.82. Found (percent) C, 56.96; H, 3.86; N, 7.67.

EXAMPLE XII

Oxidation of the appropriate 2-benzoyl-3-alkylthiomethylquinoxaline 1,4-dioxide or 2-(substituted benzoyl)-3-alkylthiomethylquinoxaline 1,4-dioxide, with 2.5 equivalents of 3-chloroperbenzoic acid, according to the procedure of Example XI, provides the following compounds:

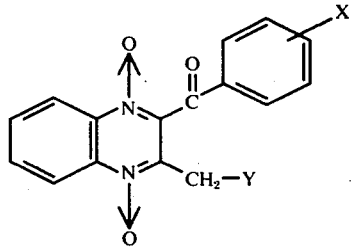

| X | Y |
|---|---|
| H | $SO_2-CH_2CH_3$ |
| H | $SO_2-CH_2CH_2CH_3$ |
| H | $SO_2-CH_2CH_2CH_2CH_3$ |
| H | $SO_2-CH_2CH_2CH(CH_3)_2$ |
| 4-OH | $SO_2-CH_3$ |
| 3-$NO_2$ | $SO_2-CH_2CH_3$ |
| 3-F | $SO_2-CH(CH_3)_2$ |
| 3-Cl | $SO_2-CH_2CH_3$ |
| 4-Br | $SO_2-CH_3$ |
| 2-$CH_3$ | $SO_2-CH_3$ |
| 4-$CH_2CH_2CH_2CH_2CH_3$ | $SO_2-CH_2CH_3$ |
| 3-$OCH_3$ | $SO_2-CH_2CH_2CH_3$ |
| 4-$OCH_3$ | $SO_2-CH_2CH(CH_3)_2$ |
| 4-$OCH_2CH_3$ | $SO_2-CH_3$ |
| 4-$OCH_2CH_2CH_2CH_2CH_3$ | $SO_2-CH_2CH_3$ |

EXAMPLE XIII

2-Benzoyl-3-methylsulfonylmethylquinoxaline 1,4-Dioxide

A solution of 3.44 g. (0.01 mol) of 2-benzoyl-3-methylsulfinylmethylquinoxaline 1,4-dioxide and 2.20 g. (0.01 mol.) of 85% pure 3-chloroperbenzoic acid in 150 ml. of chloroform is stirred at room temperature overnight. The reaction mixture is washed with 5% sodium bicarbonate solution, dried, and evaporated in vacuo to afford crude 2-benzoyl-3-methylsulfonylmethylquinoxaline 1,4-dioxide.

EXAMPLE XIV

1-Methoxy-1-phenyl-1,3dihydrofuro[3,4-b]quinoxaline 4,9-Dioxide

A stirred suspension of 0.25 g. (0.84 mmol.) of 2-benzoyl-3-hydroxy-methylquinoxaline 1,4-dioxide, in 10 ml. of methanol, was saturated with dry hydrogen chloride. The reaction mixture was stirred at room temperature overnight and then the suspended solid was collected by filtration. This afforded 0.16 g. (60% yield) of 1-methoxy-1-phenyl-1,3-dihydrofuro[3,4-b]quinoxaline 4,9-dioxide, m.p. 150°–151° C.

Analysis: Calc'd for $C_{17}H_{14}N_2O_4$(percent): C, 65.87; H, 4.55; N, 9.04; Found (percent): C, 65.08; H, 4.69; N, 8.85.

EXAMPLE XV

1-Methoxy-1-phenyl-1,3-dihydrofuro[3,4-b]quinoxaline 4,9-Dioxide

A stirred suspension of 0.50 g. (1.47 mmol.) of 2-benzoyl-3-acetoxymethylquinoxaline 1,4-dioxide in 10 ml. of methanol was saturated with dry hydrogen chloride. The reaction mixture was stirred at room temperature for three days and then the suspended solid was removed by filtration. The solid was washed with methanol, and dried, to give 0.28 g. (61% yield) of 1-methoxy-1-phenyl-1,3-dihydrofuro[3,4-b]quinoxaline 4,9-dioxide, m.p. 153 °–155° C.

EXAMPLE XVI

When the procedure of Example XV is repeated, and the quinoxaline 1,4-dioxide component used therein is:

2-benzoyl-3-hydroxymethylquinoxaline 1,4-dioxide,
2-benzoyl-3-hydroxymethylquinoxaline 1,4-dioxide,
2-benzoyl-3-hydroxymethylquinoxaline 1,4-dioxide,
2-benzoyl-3-hydroxymethylquinoxaline 1,4-dioxide,
2-(3-hydroxybenzoyl)-3-hydroxymethylquinoxaline 1,4-dioxide,
2-(2-fluorobenzoyl)-3-hydroxymethylquinoxaline 1,4-dioxide,
2-(4-nitrobenzoyl)-3-hydroxymethylquinoxaline 1,4-dioxide,
2-(3-chlorobenzoyl)-3-hydroxymethylquinoxaline 1,4-dioxide,
2-(4-chlorobenzoyl)-3-hydroxymethylquinoxaline 1,4-dioxide,
2-(4-bromobenzoyl)-3-hydroxymethylquinoxaline 1,4-dioxide,
2-(2-methylbenzoyl)-3-hydroxymethylquinoxaline 1,4-dioxide,
2-(3-isopropylbenzoyl)-3-hydroxymethylquinoxaline 1,4-dioxide,
2-(4-[pentyl]benzoyl)-3-hydroxymethylquinoxaline 1,4-dioxide,
2-(2-methoxybenzoyl)-3-hydroxymethylquinoxaline 1,4-dioxide,
2-(3-methoxybenzoyl)-3-hydroxymethylquinoxaline 1,4-dioxide,
2-(4-methoxybenzoyl)-3-hydroxymethylquinoxaline 1,4-dioxide,
2-(4-ethoxybenzoyl)-3-hydroxymethylquinoxaline 1,4-dioxide and
2-(4-[pentyloxy]benzoyl)-3-hydroxymethylquinoxaline 1,4-dioxide. respectively, and the alcohol component used therein is:

ethanol,
isopropanol,
1-butanol,
1-pentanol,
methanol,
ethanol,
methanol,
methanol,
2-butanol,
ethanol,
methanol,
ethanol,
2-pentanol
methanol,
ethanol,
2-methyl-1-butanol,
isopropanol and
methanol, respectively, this affords the following compounds:

1-ethoxy-1-phenyl-1,3-dihydrofuro[3,4-b]quinoxaline 4,9-dioxide,
1-isopropoxy-1-phenyl-1,3-dihydrofuro[3,4-b]quinoxaline 4,9-dioxide,
1-butoxy-1-phenyl-1,3-dihydrofuro[3,4-b]quinoxaline 4,9-dioxide
1-pentoxy-1-phenyl-1,3-dihydrofuro[3,4-b]quinoxaline 4,9-dioxide,
1-methoxy-1-[3-hydroxyphenyl]-1,3-dihydrofuro[3,4-b]quinoxaline 4,9-dioxide,
1-ethoxy-1-(2-fluorophenyl)-1,3-dihydrofuro[3,4-b]quinoxaline 4,9-dioxide,
1-methoxy-1-(4-nitrophenyl)-1,3-dihydrofuro[3,4-b]quinoxaline 4,9-dioxide,
1-methoxy-1-(3-chlorophenyl)-1,3-dihydrofuro[3,4-b]quinoxaline 4,9-dioxide,
1-(1-methylpropoxy)-1-(4-chlorophenyl)-1,3-dihydrofuro[3,4-b]-quinoxaline 4,9-dioxide,
1-ethoxy-1-(4-bromophenyl)-1,3-dihydrofuro[3,4-b]quinoxaline 4,9-dioxide,
1-methoxy-1-(2-tolyl)-1,3-dihydrofuro[3,4-b]quinoxaline 4,9-dioxide,
1-ethoxy-1(3-isopropylphenyl)-1,3-dihydrofuro[3,4-b]quinoxaline 4,9-dioxide,
1-(1-methylbutoxy)-1-(4-[pentyl]phenyl)-1,3-dihydrofuro[3,4-b]-quinoxaline 4,9-dioxide,
1-methoxy-1-(2-methoxyphenyl)-1,3-dihydrofuro[3,4-b]quinoxaline 4,9-dioxide,
1-ethoxy-1-(3-methoxyphenyl)-1,3-dihydrofuro[3,4-b]quinoxaline 4,9-dioxide,
1-(2-methylbutoxy)-1-(4-methoxyphenyl)-1,3-dihydrofuro[3,4-b]quinoxaline 4,9-dioxide,
1-isopropoxy-1-(4-ethoxyphenyl)-1,3-dihydrofuro[3,4-b]quinoxaline 4,9-dioxide and
1-methoxy-1-(4-[pentyloxy]phenyl)-1,3-dihydrofuro[3,4-b]-quinoxaline 4,9-dioxide, respectively.

PREPARATION A

2-Benzoyl-3-methylquinoxaline 1,4-Dioxide

To a stirred suspension of 80 g. (0.59 mol.) of benzofurazan 1-oxide and 95 g. (0.59 mol.) of benzoylacetone in 1,000 ml. of ethanol was added 1.6 g. (0.04 mol.) of finely divided sodium hydroxide. The mixture became clear after about 30 minutes. Stirring was continued for a further 16 hours, and then the solid which had precipitated was collected by filtration. It was washed with ethanol, and dried to afford 153 g. (92% yield) of 2-benzoyl-3-methylquinoxaline 1,4-dioxide, m.p. 229°–231° C.

PREPARATION B

The procedure of Preparation A is repeated, except that the benzoylacetone used therein is replaced by an equimolar amount of the appropriately substituted benzoylacetone. This produces the following compounds;

2-(3-hydroxybenzoyl)-3-methylquinoxaline 1,4-dioxide,
2-(4-hydroxybenzoyl)-3-methylquinoxaline 1,4-dioxide,
2-(3-nitrobenzoyl)-3-methylquinoxaline 1,4-dioxide,
2-(4-nitrobenzoyl)-3-methylquinoxaline 1,4-dioxide,
2-(2-fluorobenzoyl)-3-methylquinoxaline 1,4-dioxide,
2-(3-chlorobenzoyl)-3-methylquinoxaline 1,4-dioxide,
2-(4-chlorobenzoyl)-3-methylquinoxaline 1,4-dioxide,
2-(4-bromobenzoyl)-3-methylquinoxaline 1,4-dioxide,
2-(2-methylbenzoyl)-3-methylquinoxaline 1,4-dioxide,
2-(3-isopropylbenzoyl)-3-methylquinoxaline 1,4-dioxide,
2-(4-[pentyl]benzoyl)-3-methylquinoxaline 1,4-dioxide,
2-(2-methoxybenzoyl)-3-methylquinoxaline 1,4-dioxide,
2-(3-methoxybenzoyl)-3-methylquinoxaline 1,4-dioxide,
2-(4-methoxybenzoyl)-3-methylquinoxaline 1,4-dioxide,
2-(4-ethoxybenzoyl)-3-methylquinoxaline 1,4-dioxide,
2-(4-[pentyloxy]benzoyl)-3-methylquinoxaline 1,4-dioxide,
2-(4-[3-methylbutoxy]benzoyl)-3-methylquinoxaline 1,4-dioxide,
2-(2-ethylbenzoyl)-3-methylquinoxaline 1,4-dioxide,
2-(4-isopropylbenzoyl)-3-methylquinoxaline 1,4-dioxide and
2-(3-fluorobenzoyl)-3-methylquinoxaline 1,4-dioxide, respectively.

PREPARATION C

2-Benzoyl-3-bromomethylquinoxaline 1,4-Dioxide

To a stirred suspension of 28 g. (0.10 mol.) of 2-benzoyl-3-methylquinoxaline 1,4-dioxide in 1,000 ml. of methanol was added 5.6 ml. (0.11 mol.) of bromine. The reaction mixture was refluxed for 2 hours and then an additional 5.6 ml. (0.11 mol.) of bromine was added. The mixture was refluxed for an additional 2 hours and then it was cooled to 25° C. The solid which had precipitated was collected by filtration, washed with methanol, and dried to afford 30.4 g.(85% yield) of 2-benzoyl-3-bromomethylquinoxaline 1,4 -dioxide, m.p. 183°–185° C.

Analysis: Calc'd for $C_{16}H_{11}N_2O_3Br$ (percent): C, 53.53; H, 3.09; N, 7.80; Found (percent): C, 53.97; H, 3.20; N, 7.93.

PREPARATION D

The procedure of Preparation C is repeated, except that the 2-benzoyl-3-methylquinoxaline 1,4-dioxide used there is replaced by the appropriate 2-(substituted benzoyl)-3-methylquinoxaline 1,4-dioxide, to produce the following congeners.

2-(3-hydroxybenzoyl)-3-bromomethylquinoxaline 1,4-dioxide,
2-(4-hydroxybenzoyl)-3bromomethylquinoxaline 1,4-dioxide,
2-(3-nitrobenzoyl)-3-bromomethylquinoxaline 1,4-dioxide,
2-(4-nitrobenzoyl)-3-bromomethylquinoxaline 1,4-dioxide,
2-(2-fluorobenzoyl)-3-bromomethylquinoxaline 1,4-dioxide,
2-(3-chlorobenzoyl)-3-bromomethylquinoxaline 1,4-dioxide, 2-(4chlorobenzoyl)-3-bromomethylquinoxaline 1,4-dioxide,
2-(4-bromobenzoyl)-3-bromomethylquinoxaline 1,4-dioxide,
2-(2-methylbenzoyl)-3-bromomethylquinoxaline 1,4-dioxide, 2-(3-isopropylbenzoyl)-3-bromomethylquinoxaline 1,4-dioxide and 2-(4-[pentyl]benzoyl)-3-bromomethylquinoxaline 1,4-dioxide, 2-(2-methoxybenzoyl)-3-bromomethylquinoxaline 1,4-dioxide, 2-(3-methoxybenzoyl)-3-bromomethylquinoxaline 1,4-dioxide, 2-(4-methyoxybenzoyl)-3-bromomethylquinoxaline 1,4-dioxide, 2-(4-ethoxybenzoyl)-3-bromomethylquinoxaline 1,4-dioxide, 2-(4-[pentoxy]benzoyl)-3-bromomethylquinoxaline 1,4-dioxide, 2-(4-[3-methylbutoxy]benzoyl)-3-bromomethylquinoxaline 1,4-dioxide, 2-(2-ethylbenzoyl)-3-bromomethylquinoxaline 1,4-dioxide, 2-(4-isopropylbenzoyl)-3-bromomethylquinoxaline 1,4-dioxide and 2-(3-fluorobenzoyl)-3-bromomethylquinoxaline 1,4-dioxide, respectively.

What is claimed is:

1. A compound of the formula

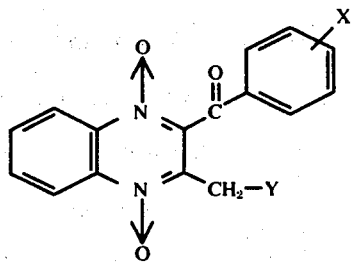

wherein X is selected from the group consisting of hydrogen, hydroxy, nitro, fluoro, chloro, bromo, alkyl having from one to five carbon atoms and alkoxy having from one to five carbon atoms;

and Y is selected from the group consisting of hydroxy, formyloxy, alkanoyloxy having from two to six carbon atoms, alkanoylthio having from two to six carbon atoms, alkylthio having from one to five carbon atoms, alkylsulfinyl having from one to five carbon atoms and alkylsulfonyl having from one to five carbon atoms.

2. A compound according to claim 1, wherein X is hydrogen.

3. The compound according to claim 2, wherein Y is hydroxy.

4. A compound according to claim 2, wherein Y is the said alkanoyloxy.

5. The compound according to claim 4, wherein Y is acetoxy.

6. A compound according to claim 2, wherein Y is the said alkanoylthio.

7. The compound according to claim 6, wherein Y is acetylthio

8. A compound according to claim 2, wherein Y is the said alkylsulfonyl.

9. The compound according to claim 8, wherein Y is methylsulfonyl.

* * * * *

Disclaimer 4,012,385.—*John P. Dirlam*, Gales Ferry, Conn. ANTIBACTERIAL QUINOXALINE 1,4-DIOXIDES. Patent dated Mar. 15, 1977. Disclaimer filed Mar. 20, 1978, by the assignee, *Pfizer Inc.*

Hereby enters this disclaimer to claims 1, 2 and 3 of said patent.

[*Official Gazette May 16, 1978.*]